US010137324B2

(12) United States Patent
Kennedy et al.

(10) Patent No.: US 10,137,324 B2
(45) Date of Patent: Nov. 27, 2018

(54) HALIDE-MEDIATED DEALKYLATION OF PHOSPHOTRIESTERS

(71) Applicant: Lawrence Livermore National Security, LLC, Livermore, CA (US)

(72) Inventors: Daniel J. Kennedy, Oakland, CA (US); Roald N. Leif, San Ramon, CA (US); Brian P. Mayer, San Francisco, CA (US); Carlos A. Valdez, San Ramon, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 0 days.

(21) Appl. No.: 15/191,431

(22) Filed: Jun. 23, 2016

(65) Prior Publication Data

US 2017/0368396 A1 Dec. 28, 2017

(51) Int. Cl.
*A62D 3/30* (2007.01)
*C07F 9/11* (2006.01)
*A62D 101/26* (2007.01)

(52) U.S. Cl.
CPC .............. *A62D 3/30* (2013.01); *C07F 9/11* (2013.01); *A62D 2101/26* (2013.01)

(58) Field of Classification Search
CPC .......... A62D 3/30; A62D 2101/26; C07F 9/11
USPC ....................................................... 588/313
See application file for complete search history.

(56) References Cited

U.S. PATENT DOCUMENTS

| 7,429,556 B2 | 9/2008 | Delcomyn et al. | |
| 2010/0176351 A1* | 7/2010 | Ruoff | B82Y 30/00 252/510 |
| 2014/0272134 A1* | 9/2014 | Roy | B01D 71/56 427/244 |

OTHER PUBLICATIONS

ATSDR, "Phosphate Ester Flame Retardants—ToxFAQs," Agency for Toxic Substances and Disease Registry, retrieved from https://www.atsdr.cdc.gov/toxfaqs/tfacts202.pdf, Oct. 2012, pp. 1-2.
Butala et al., "Dealkylation of chemical weapon agents and pesticides with group 13 Salen compounds," Main Group Chemistry, vol. 9, 2010, pp. 315-335.
Green Chemistry and Green Engineering, "5. Green Chemistry and Hazardous Organic Solvents. Green Solvents, Replacement and Alternative Techniques," Chapter 5, retrieved from http://www.chemistry.upatras.gr/hgcn/attachments/article/13/valavanidis%20gc_book_en.pdf, 2012, pp. 81-96.
Accustandard, "Phosphate Flame Retardants (PFRs)," Spotlight, Analytical Reference Standards, retrieved from http://www.vogel-gmbh.ch/accustandard/pdf/new_products/PFR%20Spotlight.pdf on May 10, 2016, 2 pages.
Srinivas et al., "Alkaline Hydrolysis Process for Treatment and Disposal of Purex Solvent Waste," Bhabha Atomic Research Centre, 1994, pp. 1-33.
Reilly, V. J., "The Hydrolysis of Tributyl Phosphate and its Effect on the Purex Process," Oak Ridge National Laboratory Technical Report ORNL 1138, 1951, 23 pages.
Moffat et al., "Basic Studies of Chemical Stability in Extraction Systems I. The Effect of Zirconium Nitrate and Nitric Acid Upon the Chemical Stability of Tributyl Phosphate," Phillips Petroleum Company IDO-14543, AEC Research and Development Report, Chemical Separations Processes, Apr. 14, 1961, pp. 1-19.
Nancharaiah et al., "Biodegradation of tributyl phosphate, an organosphate triester, by aerobic granular biofilms," Journal of Hazardous Materials, vol. 283, 2015, pp. 705-711.
Lloyd et al., "Alpha Radiolysis and Other Factors Affecting Hydrolysis of Tributyl Phosphate," Oak Ridge National Laboratory, Technical Report ORNL/TM-9565, Jun. 1985, 30 pages.
Streitwieser, A. Jr., "Solvolytic Displacement Reactions at Saturated Carbon Atoms," Department of Chemistry and Chemical Engineering, University of California, Berkeley, Mar. 1956, pp. 571-752.
Mitra et al., "Group 13 chelates in nerve gas agent and pesticide dealkylation," New Journal of Chemistry, vol. 32, Mar. 2008, pp. 783-785.
Badawi et al., "Degradation of Pesticides Wastewater by Silyl Based Cationic Surfactants," Journal of Surfactants and Detergents, vol. 10, 2007, pp. 103-108.
Morita et al., "Dealkylation Reaction of Acetals, Phosphonate, and Phosphate Esters with Chlorotrimethylsilane/Metal Halide Reagent in Acetonitrile and Its Application to the Synthesis of Phosphonic Acids and Vinyl Phosphates," Bulletin of the Chemical Society of Japan, vol. 54, Jan. 1981, pp. 267-273.

* cited by examiner

*Primary Examiner* — Edward M Johnson
(74) *Attorney, Agent, or Firm* — Zilka-Kotab

(57) ABSTRACT

In one embodiment, a method includes contacting a phosphotriester and a halogen salt in a polar solvent. In another embodiment, a method for dealkylating tributylphosphate includes contacting tributylphosphate and a halogen salt in a polar solvent.

21 Claims, 9 Drawing Sheets

Phosphotriester        Phosphodiester     $R^3$-alkyl halide

TBP                      DBP       1-iodobutane

| Name | Structure | Name | Structure |
|---|---|---|---|
| Trimethyl phosphate | 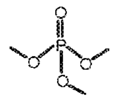 | Tripentyl phosphate | 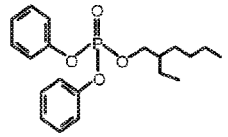 |
| Dimethyl phosphate | 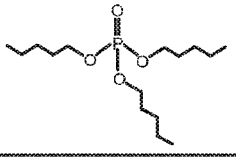 | tris(2-Ethylhexyl) phosphate | 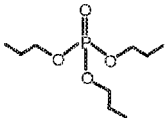 |
| Triethyl phosphate | 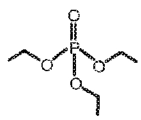 | Triphenyl phosphate | 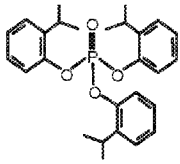 |
| Diethyl phosphate (mono & di) | 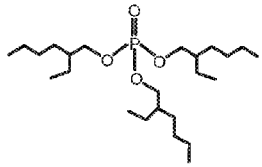 | Ethylhexyl diphenyl phosphate | 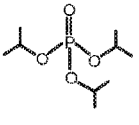 |
| Tripropyl phosphate | 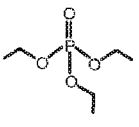 | tris (2-Isopropylphenyl) phosphate | 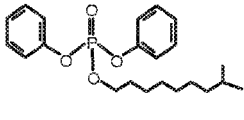 |
| Triisopropyl phosphate | 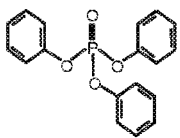 | Isodecyl diphenyl phosphate | 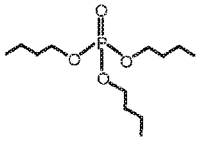 |
| Tributyl phosphate (TBP) | 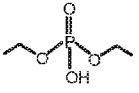 | Cresyl diphenyl phosphate | 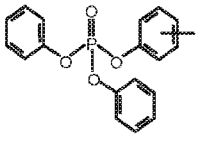 |

FIG. 2A

| Name | Structure | Name | Structure |
|---|---|---|---|
| Tri-o-cresyl phosphate | 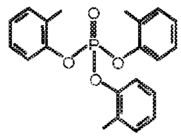 | tris (1-Chloro-2-propyl) phosphate | 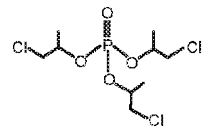 |
| Tri-p-cresyl phosphate | 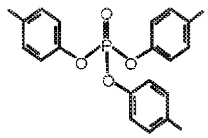 | tris (2-Chloropropyl) phosphate | 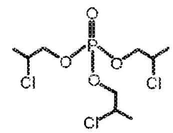 |
| Tricresyl phosphate (mix of isomers) | 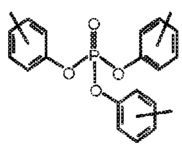 | tris (3-chloropropyl) phosphate | 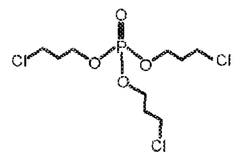 |
| Tri-m-cresyl phosphate | 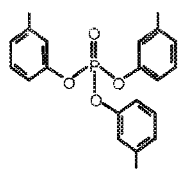 | tris (1,3-Dichloro-2-propyl) phosphate | 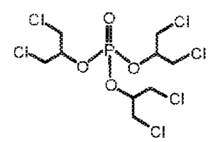 |
| tris (2-Butoxyethyl) phosphate | 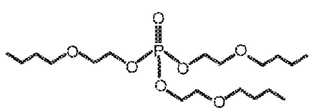 | tris (2,3-Dibromopropyl) phosphate | 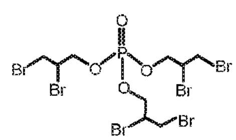 |
| tris (2-Chloroethyl) phosphate | 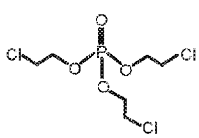 | bis (2,3-Dibromopropyl) phosphate | 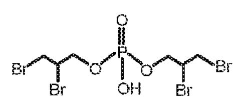 |

FIG. 2B

| Name | Structure |
|---|---|
| Tris(Tribromoneopentyl) phosphate | 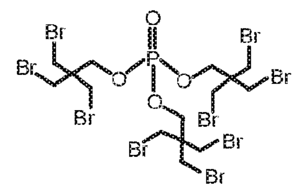 |
| Tetrakis(2-Chloroethyl) dichloro-isopentyl diphosphate | 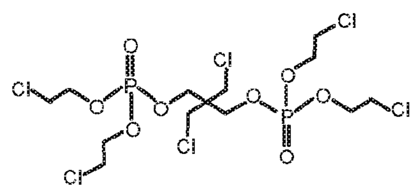 |
| Resorcinol bis(diphenyl phosphate) | 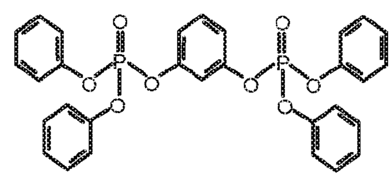 |
| Bisphenol A bis(diphenyl phosphate) | 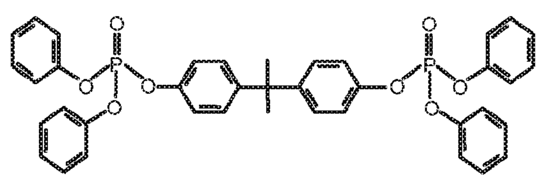 |

FIG. 2C

| KI equivalents | k (1/h) | $t_{1/2}$ (h) |
| --- | --- | --- |
| 0 | 0.00030 ± 0.00002 | 2333 ± 127 |
| 1 | 0.0861 ± 0.0027 | 8.04 ± 0.25 |
| 3 | 0.147 ± 0.013 | 4.72 ± 0.41 |
| 4.5 | 0.179 ± 0.007 | 3.87 ± 0.15 |

FIG. 5

HALIDE-MEDIATED DEALKYLATION OF PHOSPHOTRIESTERS

The United States Government has rights in this invention pursuant to Contract No. DE-AC52-07NA27344 between the United States Department of Energy and Lawrence Livermore National Security, LLC for the operation of Lawrence Livermore National Laboratory.

FIELD OFT INVENTION

The present invention relates to halide ion-mediated dealkylation of phosphotriesters.

BACKGROUND

Tributylphosphate (TBP) is a trisubstituted ester of phosphoric acid that plays a central role in numerous industrial processes. TBP is employed in flame retardant formulations, as a lubricant, and as a solvent in the synthesis of nitrocellulose used in the production of plastic films and as a binder in ink films and wood coatings. TBP is also employed in the agricultural chemistry field as a carrier solvent and defoaming agent in a variety of pesticide and herbicide formulations. Its most notable application is as a means of extracting valuable actinide metals (such as uranium and plutonium for nuclear power applications) from ores or waste through the Plutonium Uranium Redox Extraction (PUREX) process which uses a combination of TBP and a hydrocarbon-rich matrix as a solvent for extraction and purification of actinide metals. Because no viable alternatives to TBP currently exist for this application and because the International Atomic Energy Agency currently expects worldwide nuclear power usage to increase by 17% to 94% by the year 2030 there will be an increasing demand for this hazardous material for the foreseeable future. Thus, environmentally-friendly, or "green", disposal and neutralization methods targeting this chemical are necessary.

Tributylphosphate (TBP) is highly toxic and has an innate chemical stability that renders its destruction and disposal difficult thus resulting in its unwelcome and harmful persistence in the environment. Currently, methods to dispose of TBP are expensive, inefficient and the methods themselves are harmful to the environment. Incineration is the most employed technique for the breakdown of TBP into its elemental components, but must occur at high temperatures, up to 300° C. and, thus, is not cost effective. Alternative methods have been sought, but all remain expensive and thus are unrealistic for use. Acid and basic processes to dispose of TBP also require high temperatures and hazardous conditions (high acidity or alkalinity). Radioactive destruction methods of TBP are inherently hazardous and expensive. And finally, biological approaches to break down TBP involve a water-like environment which is ineffective for the oily mixture of TBP generated in the PUREX process. Moreover, degradation and disposal of phosphotriesters other than TBP suffer from similar challenges.

Accordingly, it would be desirable to efficiently convert TBP and/or other phosphotriesters to their more water-soluble salts (using, e.g. potassium, sodium, etc. as the counter-cation). In the case of TBP, it would be desirable to convert TBP to water-soluble salts, such as potassium dibutylphosphate (DBP) and potassium monobutylphosphate (MBP), using a method that is cost effective and not harmful to the environment.

SUMMARY

In one embodiment, a method includes contacting a phosphotriester and a halogen salt in a polar solvent. In another embodiment, a method for dealkylating tributylphosphate includes contacting tributylphosphate and a halogen salt in a polar solvent.

Other aspects and advantages of the present invention will become apparent from the following detailed description, which, when taken in conjunction with the drawings, illustrate by way of example the principles of the invention.

BRIEF DESCRIPTION OF THE DRAWINGS

For a fuller understanding of the nature and advantages of the present invention, as well as the preferred mode of use, reference should be made to the following detailed description read in conjunction with the accompanying drawings.

FIG. 2A-C are structures of phosphotriesters according to various embodiments of the method.

FIG. 5 is a table of the pseudo first-order rate constants and half-lives for degradation of TBP in DMSO at varying quantities of KI.

DETAILED DESCRIPTION

Figure 1A:
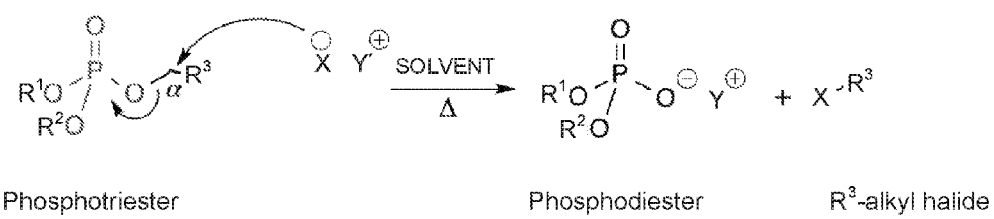
FIG. 1A is a simplified schematic drawing of one embodiment of a method for the degradation of phosphotriesters in the presence of halide ions in a polar solvent.

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include plural referents unless otherwise specified.

The following description discloses several preferred embodiments of halide dealkylation of phosphotriesters and/or related systems and methods.

In one general embodiment, a method includes contacting a phosphotdester and a halogen salt in a polar solvent.

In another general embodiment, a method for dealkylating tributylphosphate includes contacting tributylphosphate and a halogen salt in a polar solvent.

A list of acronyms used in the description is provided below.

| | |
|---|---|
| $CDCl_3$ | deuterated chloroform |
| DBP | dibutylphosphate |
| DMSO | dimethylsulfoxide |
| EI-GC/MS | electron impact gas chromatography-mass spectrometry |
| h | hours |
| HMPA | hexamethylphosphoramide |
| KI | potassium iodide |
| M | molarity |
| MBP | monobutylphosphate |
| μL | microliter |
| μs | microseconds |
| mm | millimeter |
| NMR | nuclear magnetic resonance |
| ppm | parts per million |
| PUREX | Plutonium Uranium Redox Extraction |
| R | alkyl group |
| $S_N2$ | substitution nucleophilic bimolecular |
| TBP | tributylphosphate |
| $t_{1/2}$ | half-life |

There is a need for an efficient inexpensive, and environmentally friendly method to destroy and dispose of phosphotriesters, for example tributylphate (TBP). The presently disclosed inventive concepts provide a methodology that employs a halide, e.g., the inexpensive salt potassium iodide (KI), to effectively achieve the conversion of a phosphotriester such as TBP into a more water-soluble byproduct, e.g., the potassium salts of dibutylphosphate (DBP) and monobutylphosphate (MBP). Such technique may thus represent a first step in the overall degradation of TBP to phosphoric acid.

Interestingly, the proposed mechanism counters conventional expectations that the innate chemical stability of TBP would require harsh basic or acidic conditions to break down the molecule to a water-soluble DBP byproduct. Unexpectedly, the mild conditions of using the mild potassium iodide salt in a similarly inexpensive, abundant, and environmentally friendly ("green") solvent dimethylsulfoxide (DMSO) efficiently degraded TBP into its water soluble byproducts of potassium DBP and monobutylphosphate (MBP) salts. This discovery has led to the following methodology for processing, e.g., degrading, phosphotriesters.

Figure 1B:
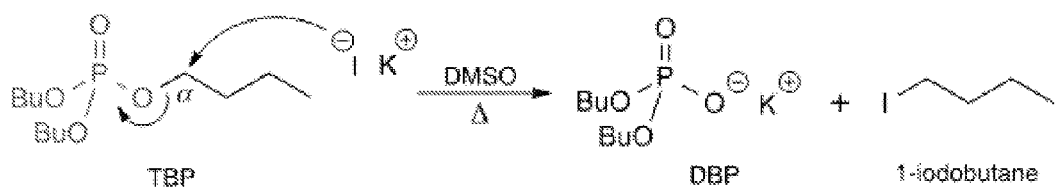
FIG. 1B is a simplified schematic drawing of one embodiment of a method for the degradation of TBP with potassium iodide in dimethylsulfoxide (DMSO).

FIGS. 1A and 1B show methods 100, 150 for the dealkylation of a phosphotriester, in accordance with one embodiment. As an option, the present method 100 may be implemented to methods such as those shown in the other FIGS. described herein. Of course, however, these methods 100, 150 and others presented herein may be used to degrade phosphotriesters which may or may not be related to the illustrative embodiments listed herein. Further, the methods presented herein may be carried out in any desired environment. Moreover, more or less operations than those shown in FIGS. 1A-B may be included in methods 100, 150, according to various embodiments. It should also be noted that any of the aforementioned features may be used in any of the embodiments described in accordance with the various methods.

FIG. 1A illustrates a method 100 that involves the degradation of a phosphotriester by contacting a phosphotriester and a halogen salt (XY) in a polar solvent. The mechanism of the $S_N2$ type reaction involves the nucleophile attacking an electrophilic center equipped with a leaving group. In the proposed scheme (FIG. 1A), the nucleophile is the halide anion ($X^-$), the electrophilic center is the α-carbon of the $R^3$ alkyl group of the phosphotriester, and the leaving group is the resulting $R^3$ alkyl halide. The nucleophilic halide ion (X) may attack the carbon of the $R^3$ alkyl group such that the phosphotriester converts to a phosphodiester associated with the positively charged ion ($Y^+$) of the halogen salt (XY) leaving the stable $R^3$-alkyl halide group.

A preferred embodiment of the method is where the phosphotriester may be tributylphosphate (TBP) and the contacting may result in the reaction as illustrated in FIG. 1B. In a preferred embodiment, the method may involve dealkylating TBP, which involves contacting TBP and a halogen salt, for example KI, in a polar solvent (DMSO) at about 100° C. In this embodiment, the iodine atom may serve a dual nature in the $S_N2$ reaction pathway as depicted in FIG. 1B, acting as both part of an outstanding leaving group (e.g. alkyl iodides) and as a formidable nucleophile in its iodide anion ($I^-$) form. The contact of TBP with KI in the presence of the polar solvent DMSO may result in conversion of the TBP to potassium DBP salt and to a lesser extent potassium MBP salt. DBP is more soluble in water than TBP and basically becomes a salt that may be disposed of easily. Thus, the product potassium DBP salt following the dealkylation of TBP with KI is not as environmentally persistent as TBP itself and may become a source of phosphorus for organisms in the soil.

Referring again to FIG. 1A, in various embodiments, the phosphotriester for dealkylation by a halide ion may be any tri-substituted ester of phosphoric acid. In one approach, any one of the phosphotriesters used as flame retardants listed in FIGS. 2A-C) may be degraded by the dealkylation method 100. In another embodiment, phosphotriesters used as lubricants may be degraded by the dealkylation of method 100. In some approaches, phosphotriesters used in the production of plastic films and as binder in ink and wood coatings may be degraded using the dealkylation method 100. In yet another approach, phosphotriesters used as a carrier solvent and defoaming agent in agricultural industries may be degraded using the dealkylation method 100. And most notably, in some approaches, TBP and phosphotriesters used in the PUREX process may be degraded using the dealkylation method 100 and/or 150.

In one embodiment, with continued reference to FIG. 1A, the alkyl groups $R^1$, $R^2$, and $R^3$ associated with the phosphotriester may be all the same. In other approaches, the alkyl groups $R^1$, $R^2$, and $R^3$ associated with the phosphotriester may be different from each other.

In a preferred embodiment, the halide component of the halogen salt involved in the dealkylation of the phosphotriester of method 100 of FIG. 1A may proceed with halide ions such as iodide, bromide, or chloride. In some approaches, the $S_N2$ reaction of the degradation of TBP as depicted in FIG. 1B may proceed with halide ions such as iodide, bromide, or chloride. With decreased nucleophilicity of the halide (for example chloride is less of a nucleophile than iodide), the reaction may proceed more slowly at the same temperature. A preferred embodiment of using iodide as the nucleophile may be desirable because of the strong nucleophilicity of the iodide ion and the abundant availability of inexpensive iodide salts.

In another embodiment of the method 100 (as depicted in FIG. 1A), the halogen salt is preferably present in at least a 1:1 molar ratio relative to the phosphotriester. Increasing the molar ratio of halogen salt may increase the rate of reaction. Accordingly, the molar ratio of halogen salt relative to the phosphotriester may be at least 2:1, at least 3:1, at least 4.5:1, etc. The limiting factor in concentration of the halide in the dealkylation of phosphotriesters may depend on the solubility of the halide in the polar solvent.

Referring to FIG. 1B, the concentration of potassium iodide dissolved in DMSO that may be effective in the dealkylation of the phosphotriester may be at least 1:1, e.g., 3:1, molar ratio with TBP, as the phosphotriester, in DMSO.

Referring again to FIG. 1A, the halogen salt of the halogen involved in the dealkylation of phosphotriesters may include any positively charged ion of Group I or Group II, or transition metals, for example, potassium, sodium, magnesium, etc. or polyatomic cations, such as ammonium.

In some approaches, the method of halide-mediated dealkylation of phosphotriesters may occur in the presence of a polar solvent that is an organic solvent capable of dissolving the halide salt used in the reaction. It is desirable for the polar solvent to dissolve the halogen salt so that the halide ion is available to degrade the phosphotriester. In one approach, the polar solvent may be a polar aprotic solvent. In a preferred embodiment of the method 100, the polar solvent may be DMSO, but may also be other polar solvents such as dimethylformamide, N-ethyl-2-pyrrolidinone (NMP), water, etc.

Furthermore, it is desirable to use a polar solvent that may not be harmful to the environment. DMSO is considered a green solvent due to its low toxicity, solubility in water, and biodegradability under environmental conditions. Moreover, the ability of DMSO to dissolve a wide variety of organic molecules and its high boiling point (189° C.) portend the applicability of this method to other persistent reagents and further elevated temperatures.

In another embodiment, the contacting of the phosphotriester and halide in polar solvent may be conducted at a temperature below a boiling point of the polar solvent. In a preferred embodiment, the high boiling point of DMSO, 189° C., allows the contacting of TBP and KI to occur at temperatures below 189° C., preferably in the range of 90° C. to 120° C. Note that degradation of TBP occurs at a faster rate at higher temperatures.

In a preferred embodiment, the dealkylation method 150 (FIG. 1B) may be applied as a method to degrade large amounts of TBP in nonpolar solvent that may be generated in nuclear waste plants during the recovery of radioactive species. The nonpolar hydrocarbon dodecane is a key diluent of TBP in the PUREX process. Other hydrocarbons that may be used in the PUREX process with TBP include other organic phases, such as a mixture of n-paraffins and/or Diesel-type mixtures enriched in hydrocarbons.

In some embodiments, the phosphotriester in method 100 of FIG. 1A may be present in a mixture of phosphotriester and a nonpolar solvent during the contacting with the halogen salt in the polar solvent. The phosphotriester may be present in any type of solvent, for example, a nonpolar solvent, a polar solvent, etc., during the contacting with a halogen salt in the polar solvent. In other words, dealkylation of the phosphotriester may occur with the phosphotriester present in any mixture of solvent as long as the halogen salt is present in a polar solvent during the contacting of the phosphotriester and the halogen salt.

Figure 3:
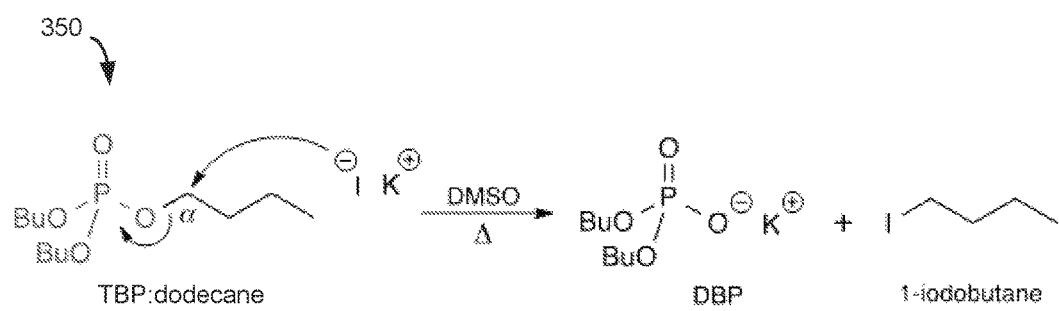
FIG. 3 is a simplified schematic drawing of one embodiment of a method for the degradation of TBP in dodecane with potassium iodide in DMSO.

In one illustrative embodiment of the dealkylation method 350 as depicted in FIG. 3, the phosphotriester TBP in the nonpolar solvent dodecane may be contacted with KI in the polar solvent DMSO. The dealkylation of TBP into DBP and MBP by KI in DMSO may occur albeit at a slower rate than contacting TBP with KI in DMSO in the absence of dodecane. Of note, dodecane may be a poor solvent for KI and for $S_N2$-type reactions in general. Elevated temperatures may not be sufficient to increase the overall collision rate of the iodide anion with TBP in dodecane alone. In addition, the two solvents, dodecane and DMSO, are immiscible solvents and the KI is insoluble in dodecane. Thus contact between the iodide and TBP may only occur at the interface of the two solvents during rigorous stirring of the combined solution.

In some approaches, DBP and MBP, the products from the dealkylation of TBP by KI in DMSO, which are present in their potassium salt forms, may be extracted into an aqueous medium, recycling the DMSO and setting up the DBP and MBP for further processing by means of oxidative hydrolysis into inorganic phosphate.

In use, the method of halide-mediated dealkylation of phosphotriesters in the presence of a polar solvent can be applied to situations in which the phosphotriester byproduct from a variety of industries is difficult to destroy and dispose. Some applications that might benefit from utilizing this method for destruction of phosphotriester waste include flame retardants, solvents used in the synthesis of nitrocellulose and production of plastic film, binder in ink films and wood coatings, as lubricant, de-foaming in herbicides and pesticides, and as an extractant in the PUREX process in the nuclear power industry.

Experimental

Methods

All reagents were of analytical grade. Tributylphosphate (TBP), dimethylsulfoxide (DMSO), dodecane, 18-crown-6, potassium iodide (KI), and hexamethylphosphoramide (HMPA) were purchased from Sigma-Aldrich (St. Louis, Mo.). Deuterated DMSO (DMSO-d6) and deuterated chloroform ($CDCl_3$) were purchased from Cambridge Isotope Laboratories (Tewksbury, Mass.).

General Procedure.

In separate 20 mL scintillation vials equipped with a stir bar, TBP (1 mL, 3.6 mmol) was taken up in either DMSO (4), dodecane (4 mL), or a 1:1 mixture of dodecane:DMSO (8 mL) and treated at ambient temperature with finely powdered potassium iodide (0, 3.6, 10.8, and 16.2 mmol, corresponding to 0, 1, 3 and 4.5 equivalents of KI to TBP). Upon addition, a slight yellow coloration was noted around the white powder in all mixtures. The vials were capped and placed in a hot plate equipped with a six-well heating block whose temperature was kept at 100±1° C. for 54 hours. The samples were continuously stirred during the experiment. Aliquots were removed at specific time points by halting the stirring process and extracting them via pipette (100 µL) into autosampler vials for analysis by nuclear magnetic resonance (NMR) and electron impact gas chromatography-mass spectrometry (EI-GC/MS). In the case of the dodecane:DMSO mixture, separate aliquots were taken of the dodecane and DMSO fractions, which quickly separated into well-defined layers after cessation of stirring. If not analyzed immediately, all aliquoted samples were kept in a refrigerator at 4° C. prior to their preparation for analysis. All experiments were conducted in duplicate.

NMR Analysis.

Spectra were obtained using a Bruker Avance III 600 MHz instrument equipped with a Balker QNP 5 mm cryoprobe (Balker Biospin, Billerica, Mass.) at 30.0±0.1° C. The pulse sequences used were default experiments provided by manufacturer. Ninety-degree pulse widths for $^1$H and $^{31}$P were manually determined via mutation experiments due to the sample matrix and pH. Pulse lengths were determined to be 18.2 µs and 9.0 µs for the proton and phosphorus channels, respectively. $^1$H-NMR (600 MHz), $^{31}$P-NMR (242 MHz), and $^{31}$P{$^1$H}-NMR signals were recorded using the deuterated solvent signal for locking. $^1$H-NMR chemical shifts were calibrated with respect to solvent deuterium chemical shifts, which are set by the spectrometer manufacturer, while all $^{31}$P-based NMR experiments were calibrated with respect to the singlet given by HMPA, which was assigned a chemical shift of 24.29 ppm. The procedure for the sample preparation involved the transfer of 50 µL of the reaction mixture into a 5 mm NMR tube followed by addition of 22 µL of a 1.8 M HMPA solution in DMSO-d6 for internal standard purposes and dilution to a total volume of 400 µL using a deuterated solvent. Samples taken from DMSO were diluted using DMSO-d6, while those taken from dodecane were diluted using CDCl$_3$.

Because $^3$P spectra are straightforward to interpret with relatively few, well-resolved resonances, this nucleus was chosen to monitor the degradation of TBP. To allow proper quantitation for the kinetics experiments, longitudinal relaxation ($T_1$) measurements were taken and values were quantified for each $^{31}$P resonance. A traditional inversion recovery pulse sequence was used, and the resulting data were described well by a single exponential growth term. The reference compound HMPA had the longest measured $T_1$ of 9.6 s, so the recycle delay (RD) was set at approximately five times $T_{1,HMPA}$ (RD=50 s) to allow for full $^{31}$P relaxation to the thermal equilibrium spin distribution. Proton inverse gated decoupling was applied via a WALTZ-16 sequence and was set to a 14.3 kHz bandwidth and was always used except when $^1$H-$^{31}$P scalar couplings were required to aid in the assignment of the various product $^{31}$P{$^1$H} peaks. For instance, coupling of the six protons attached to the three α-carbons of TBP leads to a septet in the fully coupled $^{31}$P NMR spectrum, while the four protons of DBP and two of MBP give rise to a quintet and triplet, respectively. Peak assignments were also verified by acquiring $^{31}$P{$^1$H} NMR spectra of pure TBP, DBP, and MBP. In DMSO, TBP displayed a chemical shift of −0.920 ppm which changed only slightly during reactions; DBP displayed a chemical shift which ranged from −1.035 ppm to −0.411 ppm; MBP displayed a chemical shift which ranged from −1.626 to −1.518. In dodecane, TBP displayed a chemical shift of −0.887 ppm which changed only slightly; DBP displayed a chemical shift which ranged from −1.217 ppm to −0.040 ppm; MBP was not observed in dodecane.

GC-MS Analysis.

A 7890A Agilent GC with 5975C MS detector equipped with a split/splitless injector was used for the analysis. The GC column used for the analysis was an Agilent DB-5MS capillary column (30 m×0.25 mm id×0.25 µm film thickness). Ultra-high purity helium was used as the carrier gas at 0.8 mL/min. The injector temperature was 250° C., and the injection volume was 1 µL. The oven temperature program was as follows: 40° C., held for 3 min, increased at 8° C./min to 300° C., held for 3 min. The MS ion source and quadruple temperatures were 230° C. and 150° C., respectively. Electron ionization was used with an ionization energy of 70 eV. The MS was operated to scan from m/z 29 to m/z 600 in 0.4 sec.

Data Analysis.

$^1$P{$^1$H} NMR peaks were integrated and normalized against the value of the HMPA integral (always set have an integral of exactly 100) to provide quantitation of the amount of each species present at each point in time. The TBP integrals for each experiment were fit to a pseudo-first order function of the form $I(t)=I_0\exp(-kt)$ using the non-linear least squares in the Curve Fitting Module of MATLAB 2014b (Mathworks, Inc., Natick, Mass.); here, $I(t)$ is the normalized integral at each time point, the time t is the independent variable, and the initial intensity $I_0$ and rate constant k are fitting parameters. It is worth noting that k does not describe the formation of the product DBP, since MBP is also formed during the degradation reaction.

Results and Discussion

An initial experiment involved the heating of TBP in DMSO-d6 for 54 hours at 100° C. (FIGS. 4A-D). Degradation was measured in terms of $t_{1/2}$, or half-life of original TBP concentration, which indicates the time it takes for a given concentration of TBP to decrease to one half its initial value as measured by NMR. Without any added iodide salt, TBP's background hydrolysis is almost non-existent and TBP (open circles, FIG. 4A) remained intact throughout the heating process as demonstrated by $^{31}$P-NMR ($t_{1/2}$=2330±127 h, FIG. 4A).

Figure 4A:
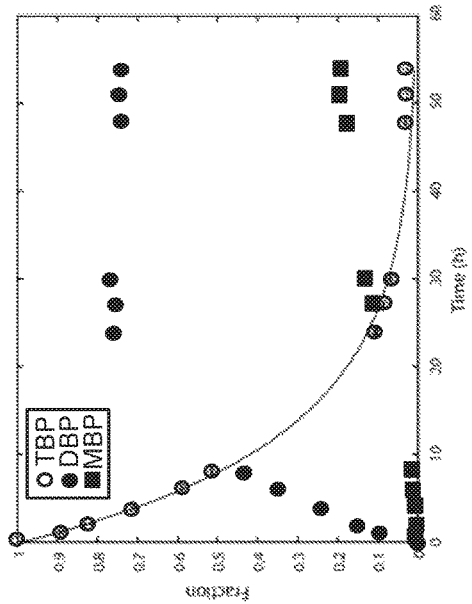
FIG. 4A is a $^{31}P\{^{1}H\}$-NMR plot graph of conversion of TBP to DBP and MBP in the presence of DMSO at 100° C. over 54 hours.
Figure 4B:
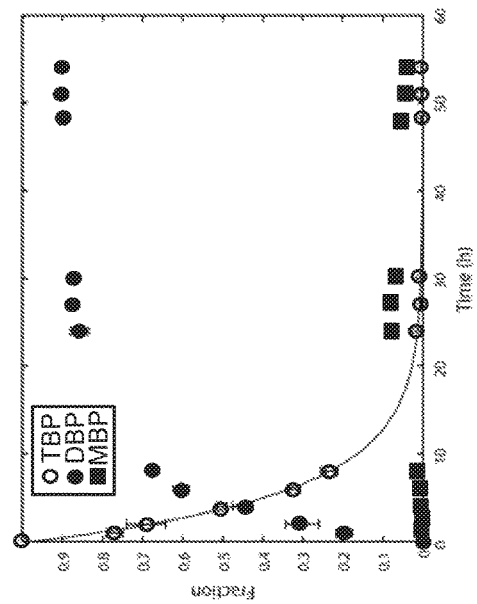
FIG. 4B is a $^{31}P\{^{1}H\}$-NMR plot graph of the conversion of TBP to DBP and MBP in the presence of 1 M equivalents of KI to TBP in DMSO.
Figure 4C:
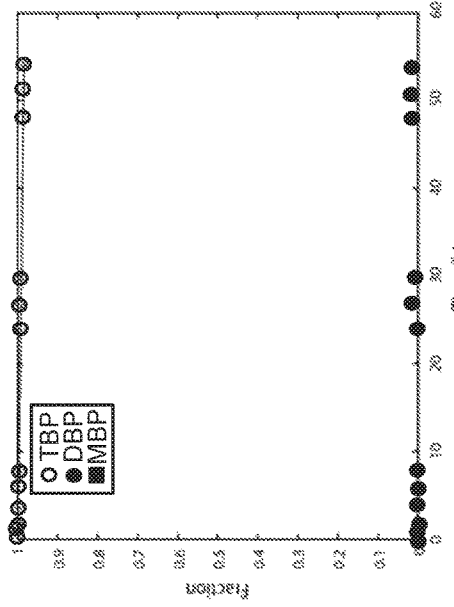
FIG. 4C is a $^{31}P\{^{1}H\}$-NMR plot graph conversion of TBP to DBP and MBP in the presence of 3M equivalents of KI to TBP in DMSO.
Figure 4D:
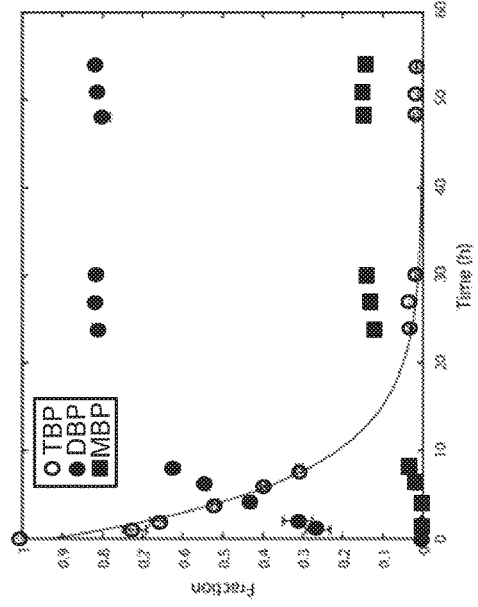
FIG. 4D is a $^{31}P\{^{1}H\}$-NMR plot graph of the conversion of TBP to DBP and MBP in the presence of 4.5 M equivalents of KI to TBP in DMSO.

In contrast, the use of one equivalent of KI resulted in the formation of DBP (solid circles, FIG. 4B) as a result of the mono-dealkylation of TBP $t_{1/2}$=8.04±0.25 h, open circles, FIG. 4B). In addition, it appears that even at one equivalent, MBP is formed (up to nearly 20% of the final reaction mixture) (solid squares, FIG. 4B). Without wishing to be bound by any theory, the inventors believe that the DBP may remain as a substrate for KI. Faster degradation of TBP to DBP and MBP was found using 3 equivalents ($t_{1/2}$=4.723±0.41 h, open circles, FIG. 4C) and 4.5 equivalents ($t_{1/2}$=3.871±0.15 h, open circles, FIG. 4D). In all cases, the solution turned yellow and then brown as the reaction proceeded. The results of the experiments in DMSO are summarized in the Table of FIG. 5 and shown in FIGS. 4A-D.

Interestingly, the use of 3 and 4.5 equivalents of KI did not lead to a 3-fold and 4.5-fold increase in the rate of TBP degradation, respectively, as would be expected from simple pseudo-first order kinetics. Without wishing to be bound by any theory, the inventors believe this discrepancy may be due to changes in pH or viscosity in the DMSO solution upon the addition of large amounts of salt. There was also the formation of small amounts of other phosphorous-containing compounds, such as a collection of pyrophosphates; in no case did the combination of all of these minor products exceed 5% of the total products formed. The nature of the products, particularly of DBP and other phosphoric acids, was based on the peak splitting patterns identified in a $^{31}$P NMR spectrum and further confirmed by EI/GC-MS analysis, after sample derivatization with N,O-bis(trimethylsilyl)trifluoroacetamide (BSTFA). The presence of 1-iodobutane in the $^1$H NMR spectrum also confirmed the KI-mediated dealkylation.

Figures 6A, 6B:
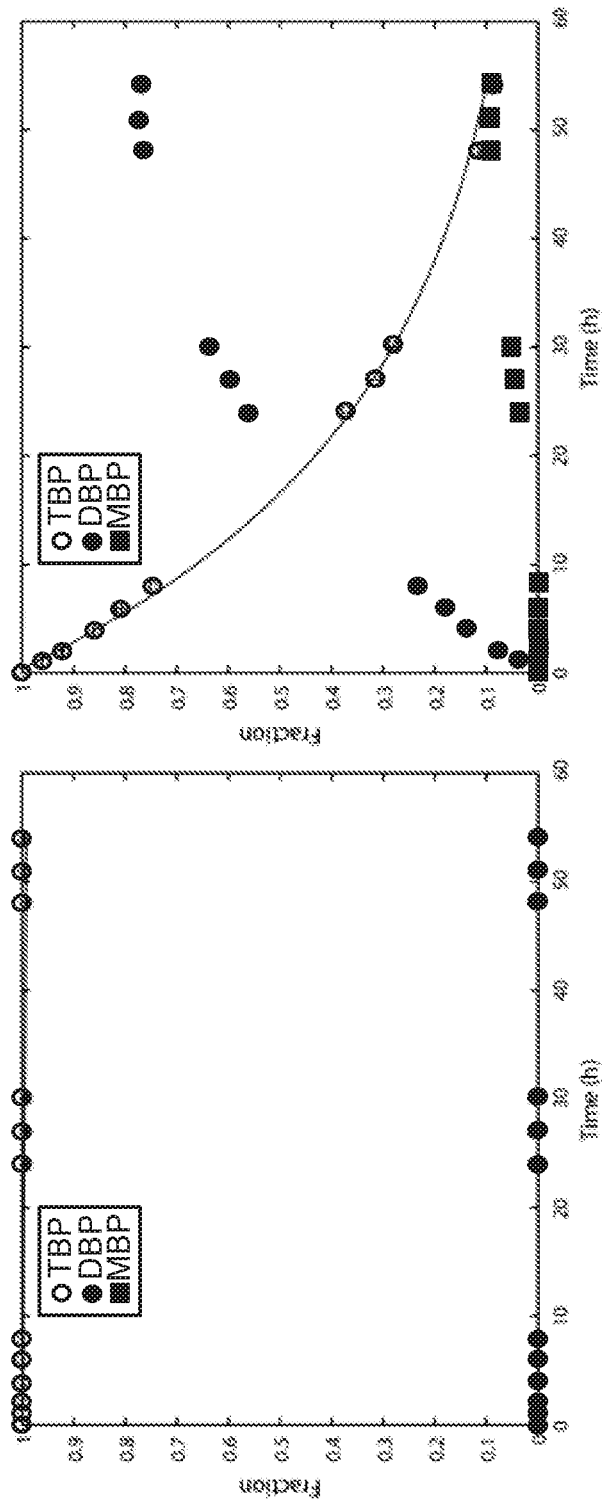
FIG. 6A is a $^{31}P$-NMR plot graph of the conversion of TBP to DBP and MBP in the presence of 1:1 DMSO: dodecane.
FIG. 6B is a $^{31}P$-NMR plot graph of the conversion of TBP to DBP and MBP in the presence of 3 M equivalents of KI to TBP in 1:1 DMSO:dodecane.

Experiments were run to determine whether iodide-mediated dealkylation might occur with TBP dissolved in the commonly used diluent dodecane as shown in FIGS. 6A-B. Dodecane is a key component in the PUREX process, either by itself or in combination with a mixture of n-paraffins and/or Diesel-type mixtures enriched in hydrocarbons. Therefore, TBP was heated in dodecane (at 100° C.) in order to assess background degradation in this medium (FIG. 6A). TBP (open circles) was found to be stable with no noticeable conversion into DBP (solid circles, FIG. 6A, no discernible DBP $^{31}$P{$^1$H} NMR signal after 54 hours). From the previous finding (FIG. 4C) that 3 equivalents of KI are sufficient to effectively yield DBP in DMSO, it was decided to heat TBP in dodecanes in the presence of KI (at 3 equivalents to TBP, FIG. 4C). This set of conditions did not differ much ($t_{1/2}$=6090±1490 h) from the seemingly non-existent background degradation in plain dodecane. A third experiment involved the use a 1:1 dodecane:DMSO mixture that was heated in the presence of KI (at 3 equivalents to TBP, FIG. 6B). In contrast to the situation in dodecane alone, degradation of TBP (open circles, FIG. 6B) into DBP (solid circles, FIG. 6B) was observed at 100° C. ($t_{1/2}$=16.2±0.4 h). Once again, the DMSO fraction of the solution turned brown as the reaction progressed. The results of the experiments in dodecane and in a 1:1 dodecane:DMSO mixture are shown in FIGS. 6A-B.

The inventors noted that dodecane and DMSO are immiscible solvents and quickly separate into layers when not being stirred. Given the insolubility of KI in dodecane, and without wishing to be bound by any theory, the inventors believe that the breakdown of TBP occurs at the interface of the two solvents. The inventors observed that the main degradation products, DBP and MBP, were significantly more soluble in DMSO than dodecane. Thus, when stirring was ceased at the end of the reaction and the two solvents were allowed to separate, the dodecane fraction was mostly free of byproducts while the degradation products were almost completely confined to the DMSO fraction.

Figure 7:
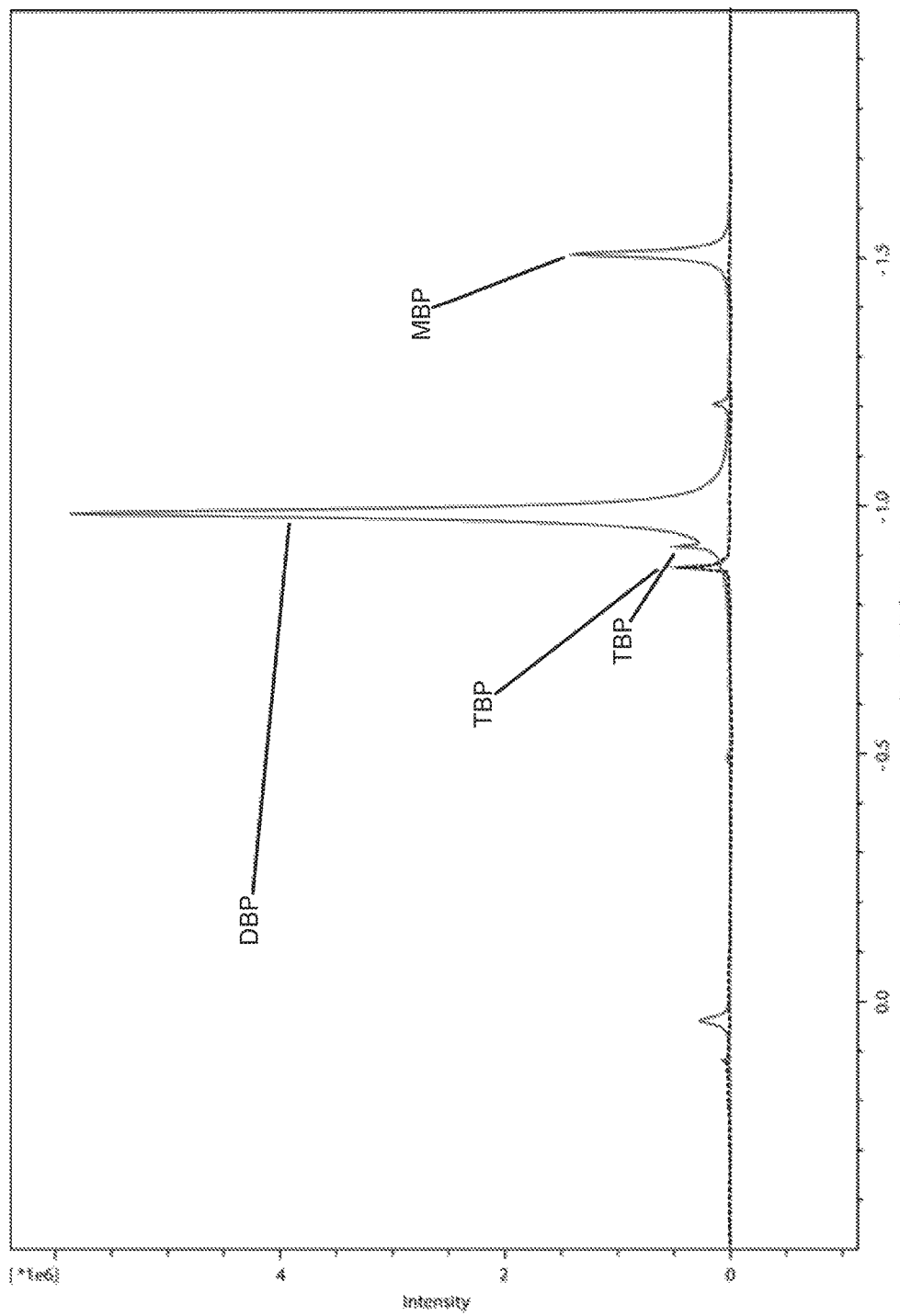
FIG. 7 is the $^{31}P\{^{1}H\}$ NMR spectra of TBP degradation products remaining in DMSO and dodecane layers after 7 days.

FIG. 7 shows $^{31}$P{$^1$H} NMR spectra of the two fractions, DMSO layer (solid line, FIG. 7) and dodecane layer (dashed line, FIG. 7), after 7 days, when the TBP NMR signal was no longer expected to be observable in either fraction. The two spectra were plotted with the same vertical scale to allow easy comparison of peak intensities. The degradation products DBP and MBP overwhelmingly preferred the DMSO layer (solid line, FIG. 7), owing to their much higher solubility in this polar aprotic solvent versus the nonpolar dodecane solvent.

Unexpectedly, small TBP peaks remain in both the DMSO layer (solid line, FIG. 7) and dodecane (dashed line, FIG. 7) fractions after 7 days. After this time, the total TBP concentration remains at approximately 2% of its initial concentration. By extrapolating the kinetics results, the value of total TBP concentration should have dropped to below 0.1% by that point in time. Without wishing to be bound by any theory, the inventors believe that this disagreement may be due to one of two effects. During this 7 day experiment, solids were deposited onto the walls of the reaction vessel as a result of stirring and heating. If significant amounts of KI were lost from solution as a result, then the pseudo-first order rate constant might decrease over time, yielding slower-than-expected degradation of TBP. This discrepancy might be mitigated by performing the reaction at a larger scale, where these surface effects are less important. Another possibility may be that the degradation reaction does not actually follow first-order kinetics at long time periods. While the precise mechanism is not known and without wishing to be bound by any theory, the inventors believe that since TBP is soluble in dodecane, the reaction most likely occurs at the DMSO:dodecane interface, movement of TBP to DMSO may constitute a rate-limiting step in the reaction. If so, the rate of reaction might be increased by the addition of more KI to the mixture as the reaction progresses.

The inventive concepts disclosed herein have been presented by way of example to illustrate the myriad features thereof in a plurality of illustrative scenarios, embodiments, and/or implementations. It should be appreciated that the concepts generally disclosed are to be considered as modular, and may be implemented in any combination, permutation, or synthesis thereof. In addition, any modification, alteration, or equivalent of the presently disclosed features, functions, and concepts that would be appreciated by a person having ordinary skill in the art upon reading the instant descriptions should also be considered within the scope of this disclosure.

While various embodiments have been described above, it should be understood that they have been presented by way of example only, and not limitation. Thus, the breadth and scope of an embodiment of the present invention should not be limited by any of the above-described exemplary embodiments, but should be defined only in accordance with the following claims and their equivalents.

What is claimed is:

1. A method, comprising:
contacting a phosphotriester and a halogen salt in a polar solvent.

2. The method of claim 1, wherein the phosphotriester is tributylphosphate.

3. The method of claim 2, wherein the contacting results in conversion of the tributylphosphate to dibutylphosphate and monobutylphosphate.

4. The method of claim 1, wherein the phosphotriester is a flame retardant.

5. The method of claim 1, wherein the phosphotriester is a lubricant.

6. The method of claim 1, wherein the phosphotriester is present in a mixture comprising the phosphotriester and a nonpolar solvent, wherein the mixture is contacted with the halogen salt in the polar solvent.

7. The method of claim 1, wherein a halide component of the halogen salt is an iodide.

8. The method of claim 1, wherein the halogen salt is present in at least a 1:1 molar ratio relative to the phosphotriester.

9. The method of claim 1, wherein the halogen salt is present in at least a 2:1 molar ratio relative to the phosphotriester.

10. The method of claim 1, wherein the halogen salt includes a Group I or Group II, or a transition metal, or a polyatomic cation.

11. The method of claim 1, wherein the polar solvent is dimethylsulfoxide (DMSO).

12. The method of claim 1, wherein the polar solvent is an organic solvent.

13. The method of claim 1, wherein the polar solvent is water.

14. The method of claim 1, wherein the contacting is conducted at a temperature below a boiling point of the polar solvent.

15. The method of claim 1, wherein the phosphotriester is present in a nonpolar solvent during the contacting with the halogen salt in the polar solvent.

16. The method of claim 1, wherein the phosphotriester is tributylphosphate, wherein the contacting results in a chemical reaction as follows:

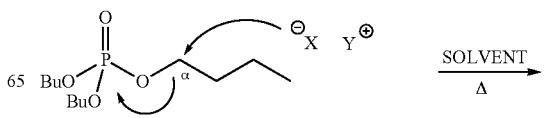

-continued

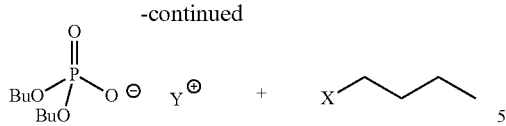

where X is a halide, and Y is a metal or polyatomic cation.

17. A method for dealkylating tributylphosphate, the method comprising:
    contacting tributylphosphate and a halogen salt in a polar solvent.

18. The method of claim 17, wherein the polar solvent is dimethylsulfoxide (DMSO).

19. The method of claim 17, wherein a halide component of the halogen salt is an iodide.

20. The method of claim 17, wherein the halogen salt is present in at least a 1:1 molar ratio relative to the tributylphosphate.

21. The method of claim 17, wherein the contacting is conducted at a temperature below a boiling point of the polar solvent.

* * * * *